United States Patent [19]

Rufer et al.

[11] 3,952,007
[45] Apr. 20, 1976

[54] PROCESSES FOR PREPARING 5-NITRO-1-METHYL-2-(2-DIALKYLAMINOVINYL)-IMIDAZOLE AND 5-NITRO-1-METHYL-2-IMIDAZOLYL CARBOXALDEHYDE

[75] Inventors: Clemens Rufer; Eberhard Schröder, both of Berlin, Germany

[73] Assignee: Schering Aktiengesellschaft, Berlin & Bergkamen, Germany

[22] Filed: Dec. 20, 1972

[21] Appl. No.: 316,928

[30] Foreign Application Priority Data
Dec. 21, 1971   Germany............................ 2164412

[52] U.S. Cl. ................... 260/309; 260/247.5 E; 260/268 H; 260/293.7; 260/296 R; 424/248; 424/250; 424/263; 424/267; 424/273
[51] Int. Cl.² .............. C07D 233/92; C07D 295/22
[58] Field of Search ................ 260/247.5 E, 268 R, 260/309, 296 R, 293.7

[56] References Cited
OTHER PUBLICATIONS
Bredereck et al., Chem. Ber., 101, No. 12, pp. 4048–4056, (1968).

Primary Examiner—Lorraine A. Weinberger
Assistant Examiner—Michael Shippen
Attorney, Agent, or Firm—Millen, Raptes & White

[57] ABSTRACT 1-substituted 5-nitro-2-(2-dialkylaminovinyl)-imidazoles having trichomonacidal activity of the formula:

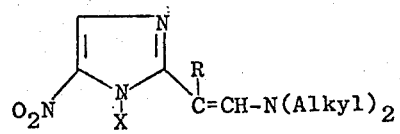

wherein R is H, $CH_3$ or $C_2H_5$ and X is hydrocarbon or hydrocarbon substituted with a halogen or a hydroxy, ether, ester or amino group, are produced by reacting the 1-substituted-5-nitro-2-alkyl-imidazoles with an aminal ester or amidoacetal of orthoformic acid or like functionally reactive derivative thereof.

6 Claims, No Drawings

PROCESSES FOR PREPARING 5-NITRO-1-METHYL-2-(2-DIALKYLAMINOVINYL)-IMIDAZOLE AND 5-NITRO-1-METHYL-2-IMIDAZOLYL CARBOXALDEHYDE

BACKGROUND OF THE INVENTION

This invention relates to novel imidazoles and more particularly to novel 1-substituted-5-nitro-2-(2-dialkylaminovinyl)-imidazoles, as well as to a process for preparing these and other imidazoles.

Nitroimidazole derivatives having useful antimicrobial properties are known in the art and have been described, for example, in German unexamined published application Nos. 1,920,150 and 1,935,685.

Several compounds of Formula II set forth hereinbelow have already been obtained by various different processes. Thus, published Dutch Patent application No. 64 13814 describes the reaction of 1-substituted 5-nitroimidazoles with paraformaldehyde in dimethyl sulfoxide in an autoclave at 110° C. over a period of 24 hours to obtain the corresponding 2-hydroxymethyl derivatives, and German unexamined published application No. 1,595,928 discloses the oxidation of the 2-hydroxymethyl compound of Formula II to the corresponding 2-formyl compound.

Due to the drastic reaction conditions, particularly the prolonged reaction times at high temperatures and elevated pressures, this process is complicated to perform, particularly on a large scale, and gives a poor yield.

Another conventional process for the production of the 1-formyl derivatives is likewise disadvantageous, especially because of the rather large number of reaction stages. For example, according to the procedure described in U.S. Pat. No. 3,549,626, benzaldehyde is reacted with 5-nitro-1,2-dimethylimidazole, water is next split off with sulfuric acid, and the aldehyde is subsequently obtained by oxidation and then immediately reacted to the thiosemicarbazone.

Both of these conventional prior art processes exhibit the additional disadvantage that the substituent at the 1-position of the imidazole ring can represent only those groups withstanding the harsh reaction conditions, e.g., alkyl and benzyloxyalkyl.

OBJECTS OF THE INVENTION

Accordingly, it is an object of this invention to provide novel 1-substituted-5-nitro-2-(2-dialkylaminovinyl)imidazoles.

Another object of this invention is to provide a relatively simple process for preparing 2-formyl and 2-alkanoyl-5-nitroimidazoles.

A more particular object of this invention is to provide a process for preparing novel 1-substituted-2-(2-dialkylaminovinyl)-imidazoles.

An additional object of this invention is to provide novel pharmaceutical compositions having antitrichomonal activity.

Upon further study of the specification and appended claims, further objects and advantages of this invention will become apparent to those skilled in the art.

SUMMARY OF THE INVENTION

The above and other objects are attained in one aspect of this invention by providing 1-substituted 5-nitro-2-(2-dialkylaminovinyl)-imidazoles of Formula I

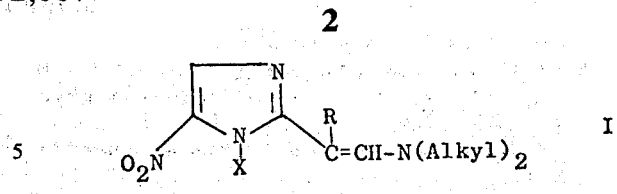

wherein R is hydrogen, methyl or ethyl; Alkyl is linear or branched alkyl of 1–4 carbon atoms; and X is alkyl of 1–6 carbon atoms or alkylene of 2–4 carbon atoms, preferably ethylene, substituted on the 2- or higher carbon atom with halogen, e.g., chlorine or bromine; hydroxy; acyloxy, e.g., alkanoyloxy of 1–5 carbon atoms, aroyloxy, e.g., benzoyloxy, 2-tetrahydropyranyloxy, or sulfonyloxy, especially alkyl or aryl sulfonyloxy, e.g., mesyloxy or tosyloxy; linear or branched dialkylamino, e.g., of 1–4 carbon atoms per alkyl group; a cyclic amino group, e.g., alkyleneamino of 5, 6 or 7 ring members whose ring carbon atoms are unsubstituted or substituted by alkyl of 1–4 carbon atoms, e.g., methyl or ethyl, and the corresponding cyclic amino groups containing a further hetero atom in the ring which can be nitrogen, oxygen or sulfur; and the acid addition salts thereof.

The invention furthermore concerns a process for the preparation of compounds of Formulae I and II set forth below, i.e., compounds of Formula III

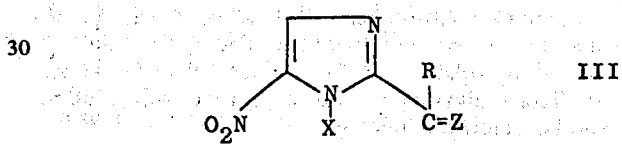

wherein Z is an oxygen atom or the group =CH—N(Alkyl)$_2$ and R, X and Alkyl have the values given above, which comprises reacting a 1-substituted 5-nitro-2-alkyl-imidazole of Formula IV

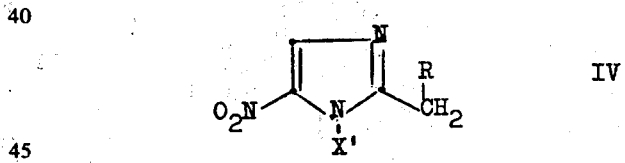

wherein R has the values given above and X' is X as defined above other than halogen, acyloxy of 1–5 carbon atoms or sulfonyloxy, is reacted with a functionally reactive derivative of orthoformic acid, e.g., an animal ester or amidoacetal thereof.

DETAILED DISCUSSION

Preferred compounds of Formula I in accordance with the present invention are those which meet one or more of the following criteria:

a. Compounds in which R is hydrogen or methyl;
b. Compounds in which alkyl is methyl or ethyl;
c. Compounds in which X is methyl or ethyl;
d. Compounds in which X is alkylene substituted by hydroxy, lower alkanoyloxy, preferably acetoxy, aroyloxy, preferably benzoyloxy; or hydrogenated pyranyloxy or furanyloxy, preferably tetrahydropyranyloxy;
e. Compounds of d in which X is substituted ethylene;
f. Compounds in which X is alkylene substituted by a substituted amino group, preferably dialkylamino, morpholino, piperidino, 4-alkyl piperazino, pyrrolidino, or hexamethyleneimino;
g. Compounds in which X is alkylene substituted by lower alkyl or aryl sulfonyloxy, preferably mesyloxy or tosyloxy;
h. Compounds in which X is alkylene substituted by pyridine;
i. Physiologically acceptable acid addition salts of groups (a)–(h), inclusive. Suitable acids for the formation of acid addition salts are, for example: hydrochloric acid, sulfuric acid, acetic acid, lactic acid, succinic acid and tartaric acid. Preferred acids are those wich form physiologically acceptable acid addition salts, but other acid addition salts can be employed for isolation, purification and/or characterization purposes.

Compounds of this invention, in addition to those shown in the Examples, include: 5-nitro-1-(2-bromoethyl)-2-(2-dimethylaminovinyl)-imidazole; 5-nitro-1-(2-chloroethyl)-2-(2-dimethylaminovinyl)-imidazole; 5-nitro-1-[2-(2-tetrahydrofuranyloxy)-ethyl]-2-(2-dimethylaminovinyl)-imidazole; 5-nitro-1-[2-(methylsulfonyloxy)-ethyl]-2-(2-dimethylaminovinyl)-imidazole; 5-nitro-1-(2-piperidino-ethyl-2-(2-dimethylaminovinyl)-imidazole; 5-nitro-1-(2-pyrrolidino-ethyl)-2-(2-dimethylaminovinyl)-imidazole; 5-nitro-1-(2-hexamethylenimino-ethyl)-2-(2-dimethylaminovinyl)-imidazole.

Examples of substituted cyclic amines include but are not limited to morpholino, 2-, 3- or 4-pyridinyl, piperidino, 2-, 3- or 4-methyl-piperidino, pyrrolidino, 2-methyl pyrrolidino or 2-, 3- or 2-,5-dimethyl-pyrrolidino, 4-alkyl-piperazino, e.g., 4-methylpiperazino, and hexamethylenimino.

The novel compounds of Formula I possess pronounced trichomonacidal activity and additionally are valuable intermediates for the production of the corresponding 2-formyl- and 2-alkanoyl-5-nitroimidazoles of Formula II:

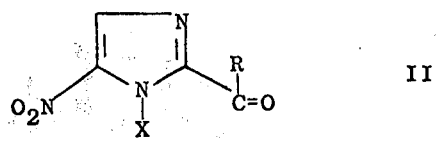

wherein R and X have the values given above. The aldehydes and ketones of general Formula II are themselves useful as intermediates for the synthesis of antimicrobial nitroimidazole derivatives. Such nitroimidazole derivatives are described, for example, in German unexamined published application Nos. 1,920,150 and 1,935,685.

The 2-formyl- and 2-alkanoyl-5-nitroimidazoles of Formula II can be prepared by oxidizing the 2-(2-dialkylaminovinyl)-imidazoles of Formula I, e.g., with ozone or alkali periodate, preferably in the presence of an osmium tetroxide catalyst.

Compounds of Formula IV defined herein are first reacted with a functionally reactive derivative of orthoformic acid, e.g., an aminal ester or amidoacetal thereof. Subsequently, a free hydroxy group is optionally converted into a sulfonic or carboxylic acid ester group or into a halide, and/or the resultant amino compounds are converted into their corresponding salts, and the thus-obtained 2-(2-dialkylaminovinyl)-imidazoles of Formula I are optionally oxidized with ozone or with an alkali periodate, preferably in the presence of an osmium tetroxide catalyst.

Suitable functionally reactive derivatives of orthoformic acid include but are not limited to the aminal esters, especially bis-dimethylamino-tert.-butoxymethane, as well as the amidoacetals, particularly the dimethylformamide diacetals, e.g., dimethylformamide dimethylacetal, dimethylformamide diethylacetal, diethylformamide diethylacetal, dimethylformamide diallyl-, dineopentyl-, dicyclohexyl-, and dibenzylacetal.

The reaction of CH-acidic compounds with derivatives of orthoformic acid is generally known from H. Bredereck et al., Chemical Reports 101: 4048–56 (1968). However, in accordance with this article, only the aminal tert.-butyl esters are capable of converting methyl heterocyclics into enamines in good yields. In contrast thereto, it has now been found that aminal esters in general, and formamidoacetals in particular, are suitable for the reaction of the present invention.

The reaction is preferably effected in an aprotic polar solvent, e.g., dimethylformamide or dimethyl sulfoxide, at an elevated temperature, e.g., 20° – 155° C., preferably 70° – 140° C. The reaction is terminated after 10–100 minutes.

The reaction product can be isolated directly from the reaction solution, optionally after removing a portion of the solvent by evaporation.

The thus-obtained dialkylaminovinyl imidazoles can be oxidized to the aldehydes and/or ketones of Formula II with ozone or with alkali periodate in the presence of catalytic amounts of osmium tetroxide.

The oxidation with alkali periodate is suitably conducted at temperatures of 10° – 60° C. for a reaction time of approximately 0.5 – 16 hours. The oxidation is effected in an aqueous medium, preferably in a water/glycol dimethyl ether mixture. Further details of this oxidation process can be found in R. Pappo et al., J. Org. Chem. 21:478 (1956).

The oxidation with ozone is conducted in a conventional manner in solvents, such as halogenated hydrocarbons, e.g., as described in J. S. Belew, Ozonization, in Oxidation (Ed. R. L. Augustine, N.Y. 1969, Marcel Dekker Inc.).

In contrast to prior art processes, the 1-substituent introduced in the 5-nitro-2-alkyl-imidazole by the process of the present application can consist of any of the desired groups described herein or their equivalents.

The reaction can also be conducted in such a manner that, after the oxidation has been accomplished, the subsequent reaction to obtain the antimicrobially effective derivatives is effected directly in the same reaction medium without intermediate separation of the oxidation product.

The compounds of Formula I are useful in the treatment of Trichomonas vaginalis infections. In this regard, they can be employed in substantially the same manner as the known compound metronidazole. For such use, they can be formulated into conventional drug forms with the additives, carrier substances, and flavoring agents customary in pharmaceutical preparations which do not deleteriously react with the effective agents, employing conventional methods. For oral application, particularly suitable are tablets, dragees, capsules, pills, suspensions and solutions. Such compositions can employ, for example, water, alcohol, polyethylene glycols, gelatin, sucrose, lactose, amylose in solutions and suspensions and magnesium stearate, talc, starch, sugars, etc., in tablets. The concentration of the effective agent in the thus-formulated compositions is dependent on the activity of the specific compound employed, the responsiveness of the individual patient and the mode of administration. Generally, they contain about 0.05 to 2.0 g., preferably about 0.05 to 0.5 g. of a compound of this invention and 0.1 to 5 g. of a pharmaceutical carrier per unit dose.

For topical application, the compounds of this invention can be applied as a powder, solution, suspension, foam or aerosol or as vaginal tablets and suppositories. For parenteral application, aqueous or oily solutions or suspensions can be used.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

5-nitro-1-methyl-2-(2-dimethylaminovinyl)-imidazole 14.1 g. (0.1 mole) of 5-nitro-1,2-dimethylimidazole and 21 g. (0.12 mole) of bis-dimethylamino-tert.-butoxymethane were heated in 90 ml. of dimethylformamide to 130° C. for 15 minutes. After cooling, the red crystals were vacuum-filtered and recrystallized from dimethylformamide.

Yield: 17 g. = 87% of theory, m.p. 193°–194° C.
UV maxima in methanol:
$\epsilon_{249} = 5,780$, $\epsilon_{297} = 15,000$, $\epsilon_{430} = 20,800$.

EXAMPLE 2

5-nitro-1-ethyl-2-(2-dimethylaminovinyl)-imidazole 15.5 g. (0.1 mole) of 5-nitro-2-methyl-1-ethylimidazole was reacted as described in Example 1; m.p. 124°–125° C.
UV maxima in methanol:
$\epsilon_{248} = 5,700$, $\epsilon_{299} = 14,900$, $\epsilon_{437} = 20,600$.

EXAMPLE 3

5-nitro-1-butyl-2-(2-dimethylaminovinyl)-imidazole 1.83 g. (0.01 mole) of 5-nitro-2-methyl-1-butylimidazole was reacted as set forth in Example 1. After removal of the solvent by evaporation, a red oil remained which, as determined by thin-layer chromatography, was uniform except for traces of starting material and exhibited the typical UV maxima in methanol:
$\epsilon_{248} = 5,680$, $\epsilon_{298} = 14,900$, $\epsilon_{435} = 20,700$.

EXAMPLE 4

5-nitro-1-methyl-2-(1-dimethylamino-2-propenyl)-imidazole 15.5 g. (0.1 mole) of 5-nitro-1-methyl-2-ethylimidazole was reacted as disclosed in Example 1, but heating the reaction mixture for 30 minutes. The residue remaining after removal of the solvent by evaporation was crystallized with ethanol; m.p. 110°–113° C.

EXAMPLE 5

5-nitro-1-[2-(4-pyridinyl)-ethyl]-2-(2-dimethylaminovinyl)-imidazole 2.32 g. (0.01 mole) of 5-nitro-2-methyl-1-[2-(4-pyridinyl)-ethyl]-imidazole was reacted analogously to Example 1. After cooling, the reaction solution was mixed with ethanol and the precipitate vacuum-filtered; m.p. 190°–191° C.
UV maxima in methanol:
$\epsilon_{256} = 7,850$, $\epsilon_{299} = 13,300$, $\epsilon_{466} = 20,400$.

EXAMPLE 6

5-nitro-1-(2-hydroxyethyl)-2-(2-dimethylaminovinyl)-imidazole 17.1 g. (0.1 mole) of 5-nitro-2-methyl-1-(2-hydroxyethyl)-imidazole was reacted as described in Example 1. After evaporation of the residue, the reaction mixture was triturated with methanol and recrystallized from isopropanol; m.p. 155°–157° C.
UV maxima in methanol:
$\epsilon_{247} = 5,590$, $\epsilon_{298} = 14,900$, $\epsilon_{438} = 20,300$.

EXAMPLE 7

5-nitro-1-(2-benzoyloxyethyl)-2-(2-dimethylaminovinyl)-imidazole 27.5 g. (0.1 mole) of 5-nitro-2-methyl-1-(2-benzoyloxyethyl)-imidazole was reacted as indicated in Example 1. After cooling, the reaction solution was mixed with ethanol, and the precipitate was vacuum-filtered; m.p. 153°–154° C.
UV maxima in methanol:
$\epsilon_{229} = 17,000$, $\epsilon_{298} = 13,400$, $\epsilon_{439} = 20,500$

EXAMPLE 8

5-nitro-1-[2-(2-tetrahydropyranyloxy)-ethyl]-2-(2-dimethylaminovinyl)-imidazole 2.54 g. (0.01 mole) of 5-nitro-2-methyl-1-[2-(2-tetrahydropyranyloxy)-ethyl]-imidazole was reacted as set out in Example 1, but heating the reaction mixture for 30 minutes. After evaporation of the solvent, the substance was obtained as a red oil having the typical UV maxima:
$\epsilon_{247} = 5,500$, $\epsilon_{299} = 13,900$, $\epsilon_{437} = 20,000$.
The starting compound was produced as follows.

17.1 g. (0.1 mole) of 5-nitro-2-methyl-1-(2-hydroxyethyl)-imidazole was refluxed with 1 g. of p-toluenesulfonic acid in 100 ml. of dihydropyran. After concentrating the reaction mixture, the latter was taken up in chloroform, washed with saturated sodium bicarbonate solution, the organic phase was concentrated, and the residue was chromatographed on 600 g. of silica gel. With benzene/acetone 2:1, 12 g. of the tetrahydropyranyl ether was obtained in the form of an oil.

EXAMPLE 9

5-nitro-1-(2-morpholinoethyl)-2-(2-dimethylaminovinyl)-imidazole 2.4 g. (0.01 mole) of 5-nitro-2-methyl-1-(2-morpholinoethyl)-imidazole and 2.1 g. (0.012 mole) of bis-dimethylaminotert.-butoxymethane were heated in 9 ml. of dimethylformamide to 130° C. for 60 minutes. After removal of the solvent by evaporation, the residue was crystallized with isopropanol; m.p. 105°–106° C.

The UV maxima were measured in methanol:
$\epsilon_{244} = 5,440$, $\epsilon_{298} = 14,500$, $\epsilon_{440} = 19,700$.
The starting compound was produced as follows.

3.25 g. (0.01 mole) of 5-nitro-2-methyl-1-(2-p-toluenesulfonyloxyethyl)-imidazole and 3.5 g. (0.04 mole) of morpholine were refluxed in 40 ml. of dimethylformamide for 35 hours. After evaporating the solvent under vacuum, the residue was mixed with sodium hydroxide solution and extracted with ethyl acetate. After extracting the ethyl acetate with hydrochloric acid, adding sodium hydroxide solution to the hydrochloric phase to a pH of 10, and renewed extraction with ethyl acetate, as well as evaporation of the solvent, the desired product was obtained which was characterized as the dihydrochloride, m.p. 225°–227° C.

EXAMPLE 10

5-nitro-1-(2-dimethylaminoethyl)-2-(2-dimethylaminovinyl)-imidazole 2.0 g. (0.01 mole) of 5-nitro-2-methyl-1-(2-dimethylaminoethyl)-imidazole was reacted as described in Example 9 and then worked up; m.p. 81°–82° C.

UV maxima in methanol:

$\epsilon_{243} = 5,390$, $\epsilon_{298} = 14,300$, $\epsilon_{438} = 19,100$.

The starting material was obtained by boiling a mixture of 3.25 g. (0.01 mole) of 5-nitro-2-methyl-1-(2-p-toluenesulfonyloxyethyl)-imidazole, 40 ml. of ethanol, and 40 ml. of a 40% aqueous dimethylamine solution for 10 hours. The reaction mixture was worked up in the same manner as described for the morpholino compound (Example 9).

EXAMPLE 11

5-nitro-1-(2-p-toluenesulfonyloxyethyl)-2-(2-dimethylaminovinyl)-imidazole 2.26 g. (0.01 mole) of 5-nitro-1-(2-hydroxyethyl)-2-(2-dimethylaminovinyl)-imidazole and 1.9 g. (0.01 mole) of p-toluenesulfochloride were agitated in 20 ml. of pyridine at 20° C. for 2 hours. Then, the mixture was poured on ice water and vacuum-filtered; m.p. 116°–118° C.

UV maxima in methanol:

$\epsilon_{226} = 16,100$, $\epsilon_{257} = 5,440$, $\epsilon_{301} = 13,100$, $\epsilon_{443} = 18,900$.

EXAMPLE 12

5-nitro-1-(2-acetoxyethyl)-2-(2-dimethylaminovinyl)imidazole 2.26 g. (0.01 mole) of 5-nitro-1-(2-hydroxyethyl)-2-(2-dimethylaminovinyl)-imidazole and 0.79 g. (0.01 mole) of acetyl chloride were reacted as described in Example 11. After pouring the reaction mixture on ice water, it was extracted with chloroform and the chloroform solution evaporated. The crude red oil exhibited the characteristic UV maxima in methanol:

$\epsilon_{245} = 5,400$, $\epsilon_{298} = 14,100$, $\epsilon_{437} = 19,900$.

EXAMPLE 13

5-nitro-1-methyl-2-(2-dimethylaminovinyl)-imidazole 14.1 g. (0.1 mole) of 5-nitro-1,2-dimethylimidazole and 14.2 g. (0.12 mole) of dimethylformamide dimethylacetal were reacted as set forth in Example 1.

Yield: 14.1 g. = 72% of theory

When conducting the reaction with diethylformamide diethylacetal in place of dimethylformamide dimethylacetal, 5-nitro-1-methyl-2-(2-diethylaminovinyl)-imidazole is obtained.

EXAMPLE 14

5-nitro-1-methyl-2-imidazolyl carboxaldehyde 1.96 g. (0.01 mole) of 5-nitro-1-methyl-2-(2-dimethylaminovinyl)-imidazole was dissolved in 100 ml. of chloroform. At −30° C., ozone (about 0.012 mole) was passed through the solution until it is decolorized. After a brief introduction of nitrogen, the cooling bath was removed and 2 g. of potassium iodide in 10 ml. of water was added; the thus-produced iodine was reduced with 2.1 g. of sodium thiosulfate in 25 ml. of water. The organic phase was worked up as usual, yielding 1.16 g. (75% of theory) of 5-nitro-1-methyl-2-imidazolyl carboxaldehyde, m.p. 93°–94° C.

EXAMPLE 15

5-nitro-1-methyl-2-imidazolyl carboxaldehyde 1.96 g. (0.01 mole) of 5-nitro-1-methyl-2-(2-dimethylaminovinyl)-imidazole and 4.28 g. (0.02 mole) of sodium periodate were suspended in 40 ml. of dimethyl glycol and 10 ml. of water and mixed with 40 mg. (0.00016 mole) of osmium tetroxide. After agitating the reaction mixture at 20° C. for 16 hours, 300 ml. of water was added thereto and the mixture extracted with chloroform; the chloroform phases were filtered over carbon and concentrated.

EXAMPLE 16

5-nitro-1-ethyl-2-imidazolyl carboxaldehyde 2.1 g. (0.01 mole) of 5-nitro-1-ethyl-2-(2-dimethylaminovinyl)-imidazole was oxidized as described in Example 15. The thus-obtained aldehyde was characterized as the oxime: Melting point: 230°–233° C.

EXAMPLE 17

5-nitro-1-(2-benzoyloxyethyl)-2-imidazolyl carboxaldehyde 3.3 g. (0.01 mole) of 5-nitro-1-(2-benzoyloxyethyl)-2-(2-dimethylaminovinyl)-imidazole was oxidized as disclosed in Example 15. Melting point: 113°–114° C.

EXAMPLE 18

5-nitro-1-(2-acetoxyethyl)-imidazole-2 carboxaldehyde 2.68 g. (0.01 mole) of 5-nitro-1-(2-acetoxyethyl)-2-(2-dimethylaminovinyl)-imidazole was oxidized as set forth in Example 15. The thus-obtained aldehyde was characterized as the oxime; m.p. 203°–205° C.

EXAMPLE 19

5-nitro-1-methyl-2-acetylimidazole 2.1 g. (0.01 mole) of 5-nitro-1-methyl-2-(1-dimethylamino-2-propenyl)-imidazole was oxidized as disclosed in Example 14. Melting point: 102°–103° C.

EXAMPLE 20

3-(5-nitro-1-methyl-2-imidazolyl)-methyleneamino-5-morpholinomethyl-2-oxazolidinone hydrochloride 1.96 g. (0.01 mole) of 5-nitro-1-methyl-2-(2-dimethylaminovinyl)-imidazole and 4.28 g. (0.02 mole) of sodium periodate were suspended in 40 ml. of dimethyl glycol and 10 ml. of water and mixed with 40 mg. (0.00016 mole) of osmium tetroxide. After 16 hours of agitation at 20° C., the mixture was combined with 11 ml. of 1N aqueous hydrochloric acid, and 2.01 g. (0.01 mole) of 3-amino-5-morpholinomethyl-2-oxazolidinone was added thereto. After maintaining the reaction mixture at 70° C. for 4 hours, it was cooled, 12 ml. of 1N aqueous sodium hydroxide solution was added, and the mixture was mixed with 40 ml. of water. The precipitate obtained by vacuum-filtering was taken up in ether, and the solution was mixed with 10 ml. of 1N methanolic hydrochloric acid. The thus-obtained product was vacuum-filtered; m.p. 238°–240° C.

EXAMPLE 21

5-nitro-1-(2-morpholinoethyl)-imidazole-2 carboxaldehyde 1.22 g. (0.0042 mole) of 5-nitro-1-(2-morpholinoethyl)-2-(2-dimethylaminovinyl)-imidazole was mixed, in 70 ml. of chloroform, with 0.31 ml. (0.0042 mole) of trifluoroacetic acid. At −30° C., the ozonization was conducted as set forth in Example 14. The ozonide was destroyed by adding 10 g. of silica gel. After the silica gel has been filtered off, the salt was extracted with water, and the free base of 5-nitro-1-(2-morpholinoethyl)-imidazole-2 carboxaldehyde was extracted with 100 ml. of ethyl acetate after adding soda. The ethyl acetate solution was refluxed together with a solution of 0.38 g. (0.0042 mole) of thiosemicarbazide in 100 ml. of ethanol and 0.46 ml. of concentrated hydrochloric acid for 20 minutes. After cooling and concentration to half the volume, 0.5 g. of the hydrochloride of the desired thiosemicarbazone was obtained by vacuum-filtering, from which the free base was produced in the usual manner; m.p. 243°–245° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a 5-nitro-1-methyl-2-(2-dialkylaminovinyl)-imidazole wherein the alkyl group is methyl or ethyl, which comprises:
   reacting 5-nitro-1,2-dimethylimidazole with a member selected from the group consisting of dimethylformamide dimethylacetal, dimethylformamide diethylacetal and diethylformamide diethylacetal to form said 5-nitro-1-methyl-2-(2-dialkylaminovinyl)-imidazole.

2. A process according to claim 1, wherein said member is dimethylformamide dimethylacetal or dimethylformamide diethylacetal.

3. A process according to claim 2, wherein said member is diethylformamide diethylacetal.

4. A process for the preparation of 5-nitro-1-methyl-2-imidazolyl carboxaldehyde, which comprises:
   a. reacting 5-nitro-1,2-dimethylimidazole with a dimethylformamide diacetal to form 5-nitro-1-methyl-2-(2-dimethylaminovinyl)-imidazole; and
   b. oxidizing the resultant 5-nitro-1-methyl-2-(2-dimethylaminovinyl)-imidazole to form said 5-nitro-1-methyl-2-imidazolyl carboxaldehyde.

5. A process according to claim 4, wherein the diacetal is dimethylacetal or diethylacetal.

6. A process according to claim 5, wherein said oxidation is effected with ozone or alkali periodate and a catalytic amount of osmium tetroxide.

* * * * *